US010919898B2

(12) United States Patent
Sand et al.

(10) Patent No.: US 10,919,898 B2
(45) Date of Patent: Feb. 16, 2021

(54) MEDICAL USE OF COMPOUND III

(71) Applicant: Boehringer Ingelheim International GmbH, Ingelheim am Rhein (DE)

(72) Inventors: Michael Steven Sand, Monroe, CT (US); Holger Rosenbrock, Mittelbiberach (DE); Riccardo Giovannini, Biberach an der Riss (DE); Masashi Adachi, Mino (JP); Bodo Betzemeier, Biberach an der Riss (DE); Tobias Brodmann, Ingelheim am Rhein (DE); Takayuki Kamata, Hyogo (JP); Yohei Kawabata, Yamagata (JP); Masanori Ito, Hyogo (JP); Daniel Marckart, Budenheim (DE); Manabu Nakatani, Hyogo (JP); Ulrike Werthmann, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 15/900,823

(22) Filed: Feb. 21, 2018

(65) Prior Publication Data

US 2018/0237445 A1 Aug. 23, 2018

Related U.S. Application Data

(60) Provisional application No. 62/462,621, filed on Feb. 23, 2017, provisional application No. 62/526,393, filed on Jun. 29, 2017.

(51) Int. Cl.
| | |
|---|---|
| *C07D 487/04* | (2006.01) |
| *A61P 25/18* | (2006.01) |
| *A61K 31/519* | (2006.01) |
| *A61K 45/06* | (2006.01) |
| *A61K 47/38* | (2006.01) |

(52) U.S. Cl.
CPC .......... *C07D 487/04* (2013.01); *A61K 31/519* (2013.01); *A61K 45/06* (2013.01); *A61K 47/38* (2013.01); *A61P 25/18* (2018.01); *C07B 2200/13* (2013.01)

(58) Field of Classification Search
CPC ....... C07D 47/04; A61P 25/18; A61K 31/519; A61K 45/06; A61K 47/38; C07B 2200/13
See application file for complete search history.

(56) References Cited

U.S. PATENT DOCUMENTS

2014/0234417 A1* 8/2014 Inoue ................... A61K 31/496 424/474

FOREIGN PATENT DOCUMENTS

| WO | 2009121919 A1 | 10/2009 | |
|---|---|---|---|
| WO | WO-2009121919 A1 * | 10/2009 | .............. A61P 25/18 |
| WO | 2010112437 A1 | 10/2010 | |
| WO | 2013110768 A1 | 8/2013 | |
| WO | 2017019723 A1 | 2/2017 | |
| WO | 2017019724 A1 | 2/2017 | |

OTHER PUBLICATIONS

International Search Report and Written Opinion for PCT/EP2018/054221 dated Apr. 28, 2018.
Salomon, Common Values in assessing health outcomes from disease and injury, The Lancet, vol. 380, 2012.
Ascher-Svanum, The cost of relapse and the predictors of relapse in the treatment of schizophrenia, BMC Psychiatry, 2010.
Lieberman, Prediction of Outcome in First Episide Pschizophrenia, J. Clin. Psychiatry, 1993.
Lieberman, Factors Influencing Treatment Response and Outcome of First-Episode Scizophrenia: Implications for Understanding the Pathophysiology of Schizophrenia, J. Clin Psychiatry, 1996.
Andreasen, Relapse Duration, Treatment Intensity, and Brain Tissue Loss in Schizophrenia: A prospective Longitudinal MRI study, Am. J. Psychiatry, 2013.
Kapur, Psychosis as a State of Aberrant Salience: A framework Linking Biology, Phenomenology, and Pharmacology, Am. J. Psychiatry, 2003.
Kapur, How antipsychotics become anti-psychotic from dopamine to salience to psychosis, Trends in Pharmacological Sciences, vol. 25, 2004.
Keefe, Early Intervention in Attenated Psychosis Syndrome, International Congress on Schizophrenia Research, 2017.
Sand, Evaluation of the Efficacy, Safety, and Tolerability of BI 409306, a novel Phosphodiesterase 9 inhibitor, International Congress in Schizophrenia Research, 2017.

* cited by examiner

*Primary Examiner* — Jeffrey S Lundgren
*Assistant Examiner* — Ibrahim D Bori
(74) *Attorney, Agent, or Firm* — David L. Kershner

(57) ABSTRACT

The present invention relates to compound III and its use for treatment and/or prevention of diseases of the schizophrenia spectrum and other psychotic disorders, first episodes of these diseases such as first episode of psychosis (FEP), relapses of these diseases such as reduction of relapse in patients with schizophrenia (REX). The invention also relates to polymorphs of compound III, and pharmaceutical compositions comprising compound III and/or its polymorphs.

4 Claims, 8 Drawing Sheets

| Table 8 | Compound III 10mg QD | | Compound III 25mg QD | | Compound III 50mg QD | | Compound III 100mg QD | | Placebo | | Total | |
|---|---|---|---|---|---|---|---|---|---|---|---|---|
| Therapy Preferred Term | N | (%) | N | (%) | N | (%) | N | (%) | N | (%) | N | (%) |
| Number of subjects [N (%)] | 87 | (100.0) | 85 | (100.0) | 85 | (100.0) | 86 | (100.0) | 173 | (100.0) | 516 | (100.0) |
| Any previous/concomitant therapy [N (%)] | 87 | (100.0) | 85 | (100.0) | 85 | (100.0) | 86 | (100.0) | 173 | (100.0) | 516 | (100.0) |
| Antipsychotics | 87 | (100.0) | 84 | (98.8) | 85 | (100.0) | 86 | (100.0) | 173 | (100.0) | 515 | (99.8) |
| Aripiprazole | 22 | (25.3) | 19 | (22.4) | 20 | (23.5) | 27 | (31.4) | 39 | (22.5) | 127 | (24.6) |
| Risperidone | 18 | (20.7) | 17 | (20.0) | 19 | (22.4) | 15 | (17.4) | 37 | (21.4) | 106 | (20.5) |
| Quetiapine fumarate | 21 | (24.1) | 15 | (17.6) | 15 | (17.6) | 17 | (19.8) | 32 | (18.5) | 100 | (19.4) |
| Olanzapine | 13 | (14.9) | 21 | (24.7) | 22 | (25.9) | 8 | (9.3) | 30 | (17.3) | 94 | (18.2) |
| Paliperidone | 2 | (2.3) | 2 | (2.4) | 8 | (9.4) | 6 | (7.0) | 8 | (4.6) | 26 | (5.0) |
| Lurasidone hydrochloride | 3 | (3.4) | 2 | (2.4) | 5 | (5.9) | 3 | (3.5) | 8 | (4.6) | 21 | (4.1) |
| Haloperidol | 2 | (2.3) | 4 | (4.7) | 1 | (1.2) | 5 | (5.8) | 8 | (4.6) | 20 | (3.9) |
| Paliperidone palmitate | 4 | (4.6) | 2 | (2.4) | 2 | (2.4) | 3 | (3.5) | 8 | (4.6) | 19 | (3.7) |
| Ziprasidone hydrochloride | 3 | (3.4) | 4 | (4.7) | 1 | (1.2) | 4 | (4.7) | 5 | (2.9) | 17 | (3.3) |
| Quetiapine | 2 | (2.3) | 3 | (3.5) | 1 | (1.2) | 1 | (1.2) | 2 | (1.2) | 9 | (1.7) |
| Ziprasidone | 2 | (2.3) | 2 | (2.4) | 1 | (1.2) | 2 | (2.3) | 2 | (1.2) | 9 | (1.7) |
| Blonanserin | 1 | (1.1) | 0 | (0.0) | 3 | (3.5) | 1 | (1.2) | 3 | (1.7) | 8 | (1.6) |

Figure 6A

| Table 8 (continued) | Compound III 10mg QD | | Compound III 25mg QD | | Compound III 50mg QD | | Compound III 100mg QD | | Placebo | | Total | |
|---|---|---|---|---|---|---|---|---|---|---|---|---|
| Blonanserin | 1 | (1.1) | 0 | (0.0) | 3 | (3.5) | 1 | (1.2) | 3 | (1.7) | 8 | (1.6) |
| Chlorpromazine hydrochloride | 1 | (1.1) | 0 | (0.0) | 1 | (1.2) | 2 | (2.3) | 3 | (1.7) | 7 | (1.4) |
| Amisulpride | 1 | (1.1) | 0 | (0.0) | 0 | (0.0) | 1 | (1.2) | 4 | (2.3) | 6 | (1.2) |
| Haloperidol decanoate | 0 | (0.0) | 2 | (2.4) | 1 | (1.2) | 1 | (1.2) | 2 | (1.2) | 6 | (1.2) |
| Lithium carbonate | 2 | (2.3) | 1 | (1.2) | 0 | (0.0) | 0 | (0.0) | 3 | (1.7) | 6 | (1.2) |
| Asenapine maleate | 1 | (1.1) | 1 | (1.2) | 0 | (0.0) | 2 | (2.3) | 0 | (0.0) | 4 | (0.8) |
| Sulpiride | 1 | (1.1) | 0 | (0.0) | 1 | (1.2) | 0 | (0.0) | 2 | (1.2) | 4 | (0.8) |
| Chlorpromazine | 2 | (2.3) | 0 | (0.0) | 0 | (0.0) | 0 | (0.0) | 0 | (0.0) | 2 | (0.4) |
| Flupentixol | 0 | (0.0) | 0 | (0.0) | 0 | (0.0) | 2 | (2.3) | 0 | (0.0) | 2 | (0.4) |
| Fluphenazine decanoate | 0 | (0.0) | 0 | (0.0) | 0 | (0.0) | 1 | (1.2) | 1 | (0.6) | 2 | (0.4) |
| Flupentixol decanoate | 0 | (0.0) | 0 | (0.0) | 0 | (0.0) | 0 | (0.0) | 1 | (0.6) | 1 | (0.2) |
| Fluphenazine | 0 | (0.0) | 0 | (0.0) | 0 | (0.0) | 0 | (0.0) | 1 | (0.6) | 1 | (0.2) |
| Fluphenazine hydrochloride | 0 | (0.0) | 0 | (0.0) | 0 | (0.0) | 1 | (1.2) | 1 | (0.6) | 1 | (0.2) |
| Iloperidone | 0 | (0.0) | 0 | (0.0) | 0 | (0.0) | 0 | (0.0) | 0 | (0.0) | 1 | (0.2) |
| Levomepromazine | 0 | (0.0) | 0 | (0.0) | 1 | (1.2) | 0 | (0.0) | 0 | (0.0) | 1 | (0.2) |

Figure 6B

| Table 8 (continued) | Compound III 10mg QD | | Compound III 25mg QD | | Compound III 50mg QD | | Compound III 100mg QD | | Placebo | | Total | |
|---|---|---|---|---|---|---|---|---|---|---|---|---|
| Levosulpiride | 0 | (0.0) | 0 | (0.0) | 0 | (0.0) | 0 | (0.0) | 1 | (0.6) | 1 | (0.2) |
| Loxapine | 1 | (1.1) | 0 | (0.0) | 0 | (0.0) | 0 | (0.0) | 0 | (0.0) | 1 | (0.2) |
| Lurasidone | 0 | (0.0) | 0 | (0.0) | 0 | (0.0) | 1 | (1.2) | 0 | (0.0) | 1 | (0.2) |
| Periciazine | 0 | (0.0) | 0 | (0.0) | 0 | (0.0) | 0 | (0.0) | 1 | (0.6) | 1 | (0.2) |
| Perospirone hydrochloride | 0 | (0.0) | 0 | (0.0) | 0 | (0.0) | 0 | (0.0) | 1 | (0.6) | 1 | (0.2) |
| Perphenazine | 1 | (1.1) | 0 | (0.0) | 0 | (0.0) | 0 | (0.0) | 0 | (0.0) | 1 | (0.2) |
| Pipamperone hydrochloride | 0 | (0.0) | 0 | (0.0) | 1 | (1.2) | 0 | (0.0) | 0 | (0.0) | 1 | (0.2) |

Figure 6C

| Table 9 | Compound III 10mg | | Compound III 25mg | | Compound III 50mg | | Compound III 100mg | | Placebo | | Total | |
|---|---|---|---|---|---|---|---|---|---|---|---|---|
| | N | (%) | N | (%) | N | (%) | N | (%) | N | (%) | N | (%) |
| System organ class/ Preferred term | | | | | | | | | | | | |
| Number of subjects | 87 | (100.0) | 85 | (100.0) | 85 | (100.0) | 86 | (100.0) | 173 | (100.0) | 516 | (100.0) |
| Psychiatric disorders | 0 | (0.0) | 0 | (0.0) | 0 | (0.0) | 0 | (0.0) | 8 | (4.6) | 8 | (1.6) |
| Schizophrenia | 0 | (0.0) | 0 | (0.0) | 0 | (0.0) | 0 | (0.0) | 5 | (2.9) | 5 | (1.0) |
| Suicidal ideation | 0 | (0.0) | 0 | (0.0) | 0 | (0.0) | 0 | (0.0) | 3 | (1.7) | 3 | (0.6) |
| Psychotic disorder | 0 | (0.0) | 0 | (0.0) | 0 | (0.0) | 0 | (0.0) | 1 | (0.6) | 1 | (0.2) |
| Percentages are calculated using total number of subjects per treatment as the denominator. | | | | | | | | | | | | |
| MedDRA version used for reporting: 19.0 | | | | | | | | | | | | |
| The sum of psychiatric disorders adds up to 8 as one subject had more than one SAE. | | | | | | | | | | | | |

Figure 7

MEDICAL USE OF COMPOUND III

FIELD OF THE INVENTION

The present invention relates to compound III for the use in the treatment of diseases of the schizophrenia spectrum and other psychotic disorders, first episodes of these diseases like first episode of psychosis (FEP), relapses of these diseases like reduction of relapse in patients with schizophrenia (REX), polymorphs of compound III, and pharmaceutical compositions comprising compound III and/or its polymorphs.

BACKGROUND OF THE INVENTION

Schizophrenia spectrum and other psychotic disorders include schizophrenia, psychosis, other psychotic disorders, and schizotypal (personality) disorder. Furthermore they include delusional disorder, attenuated psychosis syndrome, brief psychotic disorder, schizophreniform disorder, schizoaffective disorder, substance/medication-induced psychotic disorder, psychotic disorder due to another medical condition, other specified schizophrenia spectrum and other psychotic disorder, unspecified schizophrenia spectrum and other psychotic disorder, catatonia associated with another mental disorder (catatonia specifier), and catatonic disorder due to another medical condition.

They are defined by clusters of symptoms including delusions, hallucinations, disorganized thinking (speech), grossly disorganized or abnormal motor behavior (including catatonia), suicidal ideation, or negative symptoms (i.e. diminished emotional expression or avolition) such as anhedonia and social withdrawal. Suicidal behavior is sometimes in response to command hallucinations to harm oneself or others.

A first episode of psychosis is the first time a person experiences a psychotic episode.

Schizophrenia is a chronic, severe, and disabling brain disorder affecting about one percent of the world's general population. Schizophrenia affects men and women equally. It occurs at similar rates in all ethnic groups around the world. Despite advances in the treatment of schizophrenia over the past decades, the illness continues to be associated with poor outcomes. These poor outcomes are in part due to identification and intervention late in the course of the illness, thus making it more challenging to reverse.

In the Global Burden of Disease 2000 study, published in the World Health Report 2001, schizophrenia is the 7th leading cause of years lived with disability (YLDs) at global level, accounting for 2.8% of total global YLDs. Further the Disability Adjusted Life Years (DALYs), reflecting the sum of years of potential life lost due to premature mortality and the years of productive life lost due to disability is estimated at 15.6 million. In the Global Burden of Disease Study 2010", 1100 sequelae of over 220 diseases were studied: the health state with the highest disability weight was acute schizophrenia (Salomon J A, Vos T, Hogan D, Gagnon M, Naghavi M, Mokdad A, et al. Lancet 2012; 380 (9859): 2129-2143).

Due in part to the recognition of the terrible burden of established disease, the emphasis in therapy is now shifting to defining psychosis-risk syndromes and evaluating treatments that can prevent transition to psychosis in these ultra-high risk groups in addition to prompt intervention when psychosis occurs. Before the occurrence of a first episode of psychosis, those at risk for such an event also demonstrate similar symptoms at a reduced or attenuated degree and are now categorized within DSM-V as demonstrating "attenuated psychosis syndrome". A first episode is a first manifestation of the disorder meeting the defining diagnostic symptom criteria.

In subjects who progress from attenuated psychosis syndrome to their first-episode of schizophrenia, relapse rates after initial stabilization exceed 80% within five years, and the occurrence of relapse itself represents an important predictor of subsequent relapse, tripling healthcare costs in the year following (Ascher-Svanum et al. BMC Psychiatry 2010, 10:2; http://www.biomedcentral.com/1471-244X/10/2). Further, multiple relapses have been associated with poorer long-term outcome (Lieberman, J. A. (1993) Journal of Clinical Psychiatry, 54 (3 SUPPL.), pp. 13-17; Lieberman, J. A., Koreen, A. R., Chakos, M., Sheitman, B., Woerner, M., Alvir, J. Ma. J., Bilder, R. (1996) Journal of Clinical Psychiatry, 57 (SUPPL. 9), pp. 5-9; Andreasen, N. C., Liu, D., Ziebell, S., Vora, A., Ho, B.-C. (2013) American Journal of Psychiatry, 170 (6), pp. 609-615).

Relapse in schizophrenia is defined as the reoccurrence of previously treated psychotic symptoms and may include hallucinations, delusions, strong and inappropriate emotions, and disordered thought. It is also defined as any of the following: re-hospitalization for psychiatric illness, or emergency room (ER) visits for psychiatric illness, clinical worsening, or clinical worsening as assessed by Positive and Negative Syndrome Scale (PANSS), or worsening suicidal ideation and behavior as assessed by the Columbia Suicide Severity Rating Scale (C-SSRS). In the course of the illness most patients with schizophrenia experience multiple relapses which are characterized by acute psychotic exacerbation (DSM-V). Current antipsychotics do not eradicate schizophrenia spectrum, other psychotic disorders or psychotic symptoms in the majority of patients but only dampen them (Kapur S (2003) Am. J. Psychiatry 160:13-23; Kapur S (2004) Trends Pharmacol. Sci. 25:402-406).

WO 2009/121919 discloses a number of pyrazolopyrimidinones as potent PDE9 inhibitors. Among others, WO 2009/121919 discloses compound III

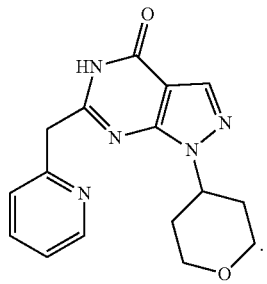

Further, WO 2009/121919 generically discloses that the compounds exemplified therein may be used in the treatment of cognitive impairment related to several diseases.

SUMMARY OF THE INVENTION

The objective technical problem underlying the present invention is thus to provide a drug substance
   which may be used in the treatment of:
      Schizophrenia spectrum and other psychotic disorders,
      Schizophrenia,
      Psychosis,
      Schizotypal (personality) disorder, Delusional disorder,
Attenuated psychosis syndrome,
Brief psychotic disorder,
Schizophreniform disorder,
Schizoaffective disorder,
Substance/Medication-Induced Psychotic Disorder,
Psychotic Disorder,
Psychotic Disorder Due to Another Medical Condition,
Other Specified Schizophrenia Spectrum and Other Psychotic Disorders,
Unspecified Schizophrenia Spectrum and Other Psychotic Disorder,
Catatonia Associated With Another Mental Disorder, or
Catatonic Disorder Due to Another Medical Condition.

In a clinical study designed to investigate compound III for the treatment of cognitive impairment associated with schizophrenia it was surprisingly found, that all serious adverse events (SAEs, 8/8) defined as psychiatric worsening occurred in the placebo arm (100% of SAEs) versus none in any active arm (see Table 9 In FIG. 7). Compared to placebo, treatment of patients with schizophrenia who are receiving antipsychotic therapy with compound III resulted in statistically significant, clinically meaningful decrease in psychiatric serious adverse events (hospitalization for serious worsening of schizophrenia symptoms) and decrease in the intensity and occurrence of suicidal ideation.

According to the present invention, compound III has surprisingly been found to fulfil the above mentioned criteria required for use in the treatment of:
Schizophrenia spectrum and other psychotic disorders,
Schizophrenia,
Psychosis,
Schizotypal (personality) disorder,
Delusional disorder,
Attenuated psychosis syndrome,
Brief psychotic disorder,
Schizophreniform disorder,
Schizoaffective disorder,
Substance/Medication-Induced Psychotic Disorder,
Psychotic Disorder,
Psychotic Disorder Due to Another Medical Condition,
Other Specified Schizophrenia Spectrum and Other Psychotic Disorders,
Unspecified Schizophrenia Spectrum and Other Psychotic Disorder,
Catatonia Associated With Another Mental Disorder, or
Catatonic Disorder Due to Another Medical Condition.

Furthermore compound III can be used in the treatment of first episodes of:
Schizophrenia spectrum and other psychotic disorders,
Schizophrenia,
Psychosis,
Schizotypal (personality) disorder,
Delusional disorder,
Attenuated psychosis syndrome,
Brief psychotic disorder,
Schizophreniform disorder,
Schizoaffective disorder,
Substance/Medication-Induced Psychotic Disorder,
Psychotic Disorder Due to Another Medical Condition,
Other Specified Schizophrenia Spectrum and Other Psychotic Disorders,
Unspecified Schizophrenia Spectrum and Other Psychotic Disorder,
Catatonia Associated With Another Mental Disorder, or
Catatonic Disorder Due to Another Medical Condition.

Furthermore compound III can be used in the treatment of relapses of:
Schizophrenia spectrum and other psychotic disorders,
Schizophrenia,
Psychosis,
Schizotypal (personality) disorder,
Delusional disorder,
Attenuated psychosis syndrome,
Brief psychotic disorder,
Schizophreniform disorder,
Schizoaffective disorder,
Substance/Medication-Induced Psychotic Disorder,
Psychotic Disorder Due to Another Medical Condition,
Other Specified Schizophrenia Spectrum and Other Psychotic Disorders,
Unspecified Schizophrenia Spectrum and Other Psychotic Disorder,
Catatonia Associated With Another Mental Disorder, or
Catatonic Disorder Due to Another Medical Condition.

Furthermore compound III can be used in the prevention/delay of:
Schizophrenia spectrum and other psychotic disorders,
Schizophrenia,
Psychosis,
Schizotypal (personality) disorder,
Delusional disorder,
Attenuated psychosis syndrome,
Brief psychotic disorder,
Schizophreniform disorder,
Schizoaffective disorder,
Substance/Medication-Induced Psychotic Disorder,
Psychotic Disorder Due to Another Medical Condition,
Other Specified Schizophrenia Spectrum and Other Psychotic Disorders,
Unspecified Schizophrenia Spectrum and Other Psychotic Disorder,
Catatonia Associated With Another Mental Disorder, or
Catatonic Disorder Due to Another Medical Condition.

Furthermore compound III can be used in the prevention/delay of first episodes and/or relapses of above mentioned diseases, conditions and symptoms.

Furthermore compound III can be used in the treatment of schizophrenia by disease stabilization, schizophrenia by reducing the severity of relapses, schizophrenia by prevention of relapses, or schizophrenia by delaying relapses.

Furthermore compound III can be used in the treatment of symptoms of above mentioned diseases, conditions and symptoms.

Accordingly compound III can be used in the treatment of:
delusions,
hallucinations,
disorganized thinking (speech),
grossly disorganized or abnormal motor behavior (including catatonia),
suicidal ideation, or
negative symptoms.

Furthermore compound III can be used in the prevention/delay of first episodes and/or relapses of above mentioned symptoms.

BRIEF DESCRIPTION OF THE SEVERAL VIEWS OF THE DRAWING

FIGS. 6A-6C (Table 8) include data showing the results of a study using antipsychotic drugs for concomitant antipsychotic therapy.

FIG. 7 includes data showing the Frequency [N (%)] of subjects with serious adverse events by treatment, primary system organ class and preferred term—treated set (TS).

DETAILED DESCRIPTION OF THE INVENTION

Figure 1:
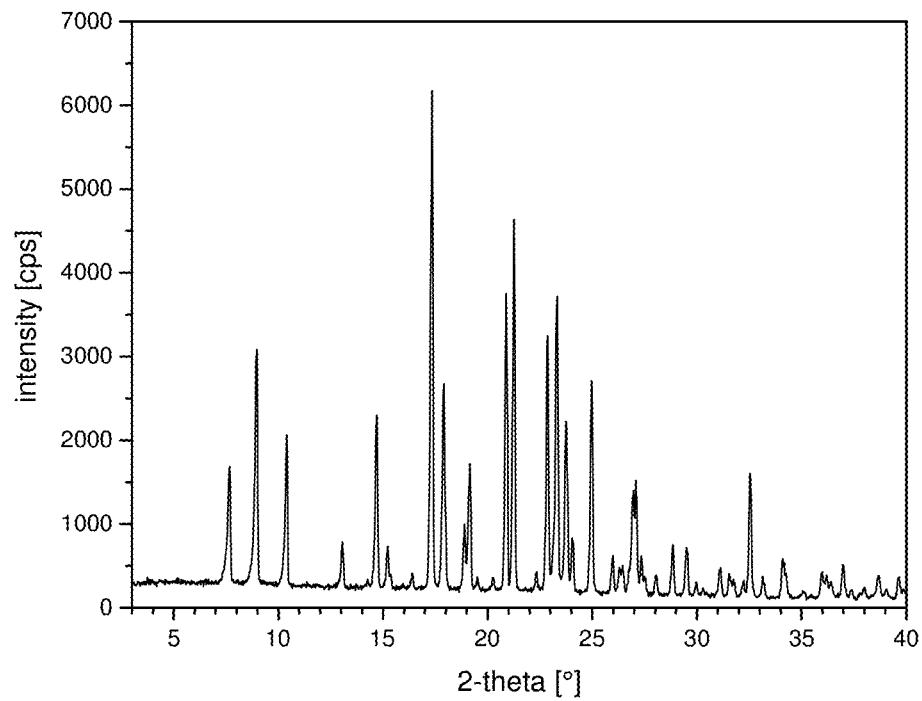
FIG. 1 shows the X-ray powder diffraction pattern of Compound IIIa.

According to a first aspect, the present invention provides compound III:

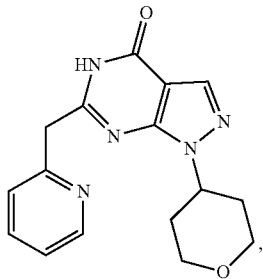

III for use in the treatment of:
Schizophrenia spectrum and other psychotic disorders,
Schizophrenia,
Psychosis,
Schizotypal (personality) disorder,
Delusional disorder,
Attenuated psychosis syndrome,
Brief psychotic disorder,
Schizophreniform disorder,
Schizoaffective disorder,
Substance/Medication-Induced Psychotic Disorder,
Psychotic Disorder,
Psychotic Disorder Due to Another Medical Condition,
Other Specified Schizophrenia Spectrum and Other Psychotic Disorders,
Unspecified Schizophrenia Spectrum and Other Psychotic Disorder,
Catatonia Associated With Another Mental Disorder, or Catatonic Disorder Due to Another Medical Condition.

According to a second aspect, the present invention provides compound III for use in the treatment of first episodes of:
Schizophrenia spectrum and other psychotic disorders,
Schizophrenia,
Psychosis,
Schizotypal (personality) disorder,
Delusional disorder,
Attenuated psychosis syndrome,
Brief psychotic disorder,
Schizophreniform disorder,
Schizoaffective disorder,
Substance/Medication-Induced Psychotic Disorder,
Psychotic Disorder Due to Another Medical Condition,
Other Specified Schizophrenia Spectrum and Other Psychotic Disorders,
Unspecified Schizophrenia Spectrum and Other Psychotic Disorder,
Catatonia Associated With Another Mental Disorder, or Catatonic Disorder Due to Another Medical Condition.

According to another aspect, the present invention provides compound III for use in the treatment of relapses of:
Schizophrenia spectrum and other psychotic disorders,
Schizophrenia,
Psychosis,
Schizotypal (personality) disorder,
Delusional disorder,
Attenuated psychosis syndrome,
Brief psychotic disorder,
Schizophreniform disorder,
Schizoaffective disorder,
Substance/Medication-Induced Psychotic Disorder,
Psychotic Disorder Due to Another Medical Condition,
Other Specified Schizophrenia Spectrum and Other Psychotic Disorders,
Unspecified Schizophrenia Spectrum and Other Psychotic Disorder,
Catatonia Associated With Another Mental Disorder, or Catatonic Disorder Due to Another Medical Condition.

According to another aspect, the present invention provides compound III for use in the prevention/delay of:
Schizophrenia spectrum and other psychotic disorders,
Schizophrenia,
Psychosis,
Schizotypal (personality) disorder,
Delusional disorder,
Attenuated psychosis syndrome,
Brief psychotic disorder,
Schizophreniform disorder,
Schizoaffective disorder,
Substance/Medication-Induced Psychotic Disorder,
Psychotic Disorder Due to Another Medical Condition,
Other Specified Schizophrenia Spectrum and Other Psychotic Disorders,
Unspecified Schizophrenia Spectrum and Other Psychotic Disorder,
Catatonia Associated With Another Mental Disorder, or Catatonic Disorder Due to Another Medical Condition.

According to another aspect, the present invention provides compound III for use in the prevention/delay of first episodes and/or relapses of above mentioned diseases, conditions and symptoms.

According to another aspect, the present invention provides compound III for use in the treatment of schizophrenia by disease stabilization, schizophrenia by reducing the severity of relapses, schizophrenia by prevention of relapses, or schizophrenia by delaying relapses.

According to another aspect, the present invention provides compound III for use in the treatment of reduction of relapse in schizophrenia.

According to another aspect, the present invention provides compound III for use in the treatment of reduction of relapse in patients with schizophrenia receiving antipsychotic therapy.

According to another aspect, the present invention provides compound III for use in the treatment of attenuated psychosis syndrome.

According to another aspect, the present invention provides compound III for use in the prevention of first episode psychosis.

According to another aspect, the present invention provides compound III for use in the prevention of first episode psychosis in individuals with attenuated psychosis syndrome.

According to another aspect, the present invention provides compound III for use in the treatment of symptoms of above mentioned diseases, conditions and symptoms.

According to another aspect, the present invention provides compound III for use in the treatment of:
delusions,
hallucinations,
disorganized thinking (speech),
grossly disorganized or abnormal motor behavior (including catatonia),
suicidal ideation, or
negative symptoms.

According to another aspect, the present invention provides compound III for use in the treatment of first episodes and/or relapses of above mentioned symptoms.

According to another aspect, the present invention provides compound III for use in the prevention/delay of first episodes and/or relapses of above mentioned symptoms.

According to another aspect, the present invention provides compound III according to any one of the preceding aspects, characterized in that compound III is administered in addition to treatment with another antipsychotic drug.

According to another aspect, the present invention provides compound III according to any one of the preceding aspects, characterized in that the antipsychotic drug is selected from the group consisting of Aripiprazole, Risperidone, Quetiapine fumarate, Olanzapine, Paliperidone, Lurasidone hydrochloride, Haloperidol, Paliperidone palmitate, Ziprasidone hydrochloride, Quetiapine, Ziprasidone, Blonanserin, Chlorpromazine hydrochloride, Amisulpride, Haloperidol decanoate, Lithium carbonate, Asenapine maleate, Sulpiride, Chlorpromazine, Flupentixol, Fluphenazine decanoate, Flupentixol decanoate, Fluphenazine, Fluphenazine hydrochloride, Iloperidone, Levomepromazine, Levosulpiride, Loxapine, Lurasidone, Periciazine, Perospirone hydrochloride, Perphenazine, Clozapine, and Pipamperone hydrochloride.

According to another aspect, the present invention provides compound III according to any one of the preceding aspects, characterized in that 10, 25, 50 or 100 mg of compound III are administered.

According to another aspect, the present invention provides compound III according to any one of the preceding aspects, characterized in that compound III is administered once or twice daily.

According to another aspect, the present invention provides compound III according to any one of the preceding aspects, characterized in that compound III is administered orally.

WO 2009/121919 discloses the synthesis of compound IIIa. Now, it has surprisingly been found that another polymorphic form, compound IIIb, exists. Both compound IIIa and compound IIIb, respectively, can be synthesized in pure form. Compound IIIa was obtained in a purity >95% (ratio between compound IIIa and compound IIIb >95:5 based on XRPD) as well as compound IIIb in a purity >95% (ratio between compound IIIb and compound IIIa >95:5 based on XRPD). Further, both compound IIIa and compound IIIb are characterized by its corresponding XRPD and Raman data.

As used herein, the term "compound IIIa" refers to crystalline form a of Compound III.

As used herein, the term "compound IIIb" refers to crystalline form b of Compound III.

The polymorphic form resulting from the synthesis according to WO 2009/121919, namely compound IIIa, shows a X-ray powder diffraction pattern comprising peaks at the following 2-theta values measured using monochromatic CuKα1 radiation of λ=1.54056 Å, 40 kV, 40 mA: 7.7°±0.2° and 9.0°±0.2°.

The polymorphic form resulting from the synthesis according to WO 2009/121919, namely compound IIIa, shows a X-ray powder diffraction pattern comprising peaks at any one or all of the following 2-theta values measured using monochromatic CuKα1 radiation of λ=1.54056 Å, 40 kV, 40 mA: 17.3°±0.2°, 21.3°±0.2°, 20.9°±0.2°, 23.3°±0.2°, 9.0°±0.2°, 14.7°±0.2°, 7.7°±0.2°.

The polymorphic form resulting from the synthesis according to WO 2009/121919, namely compound IIIa, shows a X-ray powder diffraction pattern comprising peaks at the following 2-theta values measured using monochromatic CuKα1 radiation of λ=1.54056 Å, 40 kV, 40 mA: 7.7°±0.2° and 9.0°±0.2°, and the Raman spectrum comprises peaks at any one or all of the following Raman shifts expressed in wavenumbers in $cm^{-1}$: 1190±2, 1401±2, 1675±2.

The polymorphic form resulting from the synthesis according to WO 2009/121919, namely compound IIIa, has a purity >75% (ratio between compound IIIa and compound IIIb >75:25 based on XRPD).

The polymorphic form resulting from the synthesis according to WO 2009/121919, namely compound IIIa, has a purity >90% (ratio between compound IIIa and compound IIIb >90:10 based on XRPD).

The polymorphic form resulting from the synthesis according to WO 2009/121919, namely compound IIIa, has a purity >95% (ratio between compound IIIa and compound IIIb >95:5 based on XRPD).

According to another aspect, the present invention provides compound IIIb showing a X-ray powder diffraction pattern comprising a peak at the following 2-theta value measured using monochromatic CuKα1 radiation of λ=1.54056 Å, 40 kV, 40 mA: 6.4°±0.2°.

According to another aspect, the present invention provides compound IIIb showing a X-ray powder diffraction pattern comprising peaks at any one or all of the following 2-theta values measured using monochromatic CuKα1 radiation of λ=1.54056 Å, kV, 40 mA: 20.8°±0.2°, 21.1°±0.2°, 21.6°±0.2°, 6.4°±0.2°, 23.0°±0.2°, 25.2°±0.2°, 12.9°±0.2°.

According to another aspect, the present invention provides compound IIIb showing a X-ray powder diffraction pattern comprising peaks at the following 2-theta values measured using monochromatic CuKα1 radiation of λ=1.54056 Å, 40 kV, 40 mA: 6.4°±0.2°, and the Raman spectrum comprises peaks at any one or all of the following Raman shifts expressed in wavenumbers in $cm^{-1}$: 1182±2, 1394±2, 1663±2.

According to another aspect, the present invention provides compound IIIb having a purity >10% (ratio between compound IIIb and compound IIIa >10:90 based on XRPD).

According to another aspect, the present invention provides compound IIIb having a purity >20% (ratio between compound IIIb and compound IIIa >20:80 based on XRPD).

According to another aspect, the present invention provides compound IIIb having a purity >30% (ratio between compound IIIb and compound IIIa >30:70 based on XRPD).

According to another aspect, the present invention provides compound IIIb having a purity >40% (ratio between compound IIIb and compound IIIa >40:60 based on XRPD).

According to another aspect, the present invention provides compound IIIb having a purity >50% (ratio between compound IIIb and compound IIIa >50:50 based on XRPD).

According to another aspect, the present invention provides compound IIIb having a purity >60% (ratio between compound IIIb and compound IIIa >60:40 based on XRPD).

According to another aspect, the present invention provides compound IIIb having a purity >70% (ratio between compound IIIb and compound IIIa >70:30 based on XRPD).

According to another aspect, the present invention provides compound IIIb having a purity >75% (ratio between compound IIIb and compound IIIa >75:25 based on XRPD).

According to another aspect, the present invention provides compound IIIb having a purity >80% (ratio between compound IIIb and compound IIIa >80:20 based on XRPD).

According to another aspect, the present invention provides compound IIIb having a purity >90% (ratio between compound IIIb and compound IIIa >90:10 based on XRPD).

According to another aspect, the present invention provides compound IIIb having a purity >95% (ratio between compound IIIb and compound IIIa >95:5 based on XRPD).

In another aspect, the present invention relates to compound III, compound IIIa, compound IIIb or mixtures thereof for use in the treatment of above mentioned diseases, conditions and symptoms.

Figure 5:
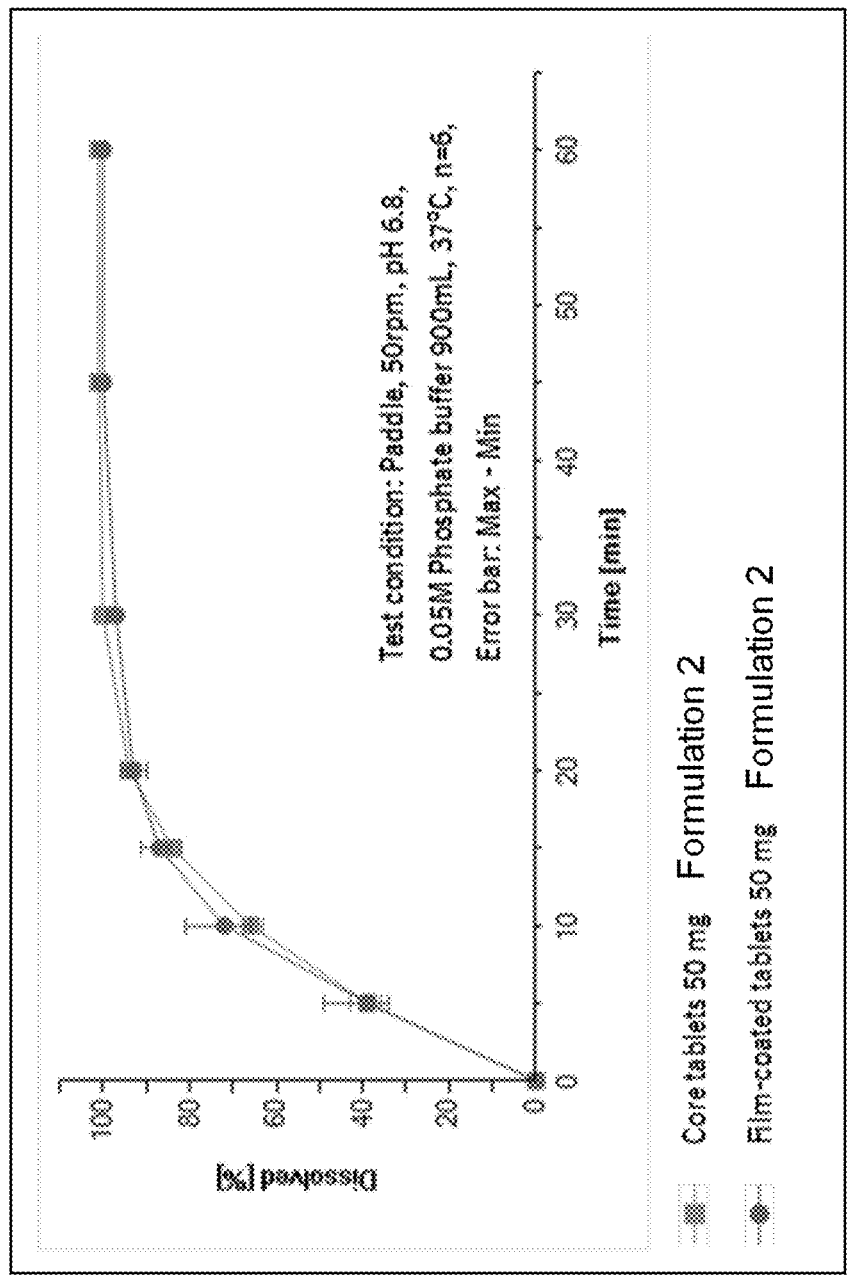
FIG. 5 shows the dissolution profiles of core tablets and film-coated tablets containing 50 mg of Formulation 2 (Table 5 and Table 6) produced from milled drug substance.

Further, it has surprisingly been found that by combining hydroxypropyl cellulose and/or croscarmellose sodium with compound III, IIIa or IIIb or a mixture thereof in a pharmaceutic composition the drug load can be adjusted to the same level for all dose strengths and a fast dissolution of the tablet can be reached irrespective of the low intrinsic dissolution rate of compound III in the physiologically relevant pH range above pH 4 (formulation 1, Table 3, and/or formulation 2, Table 5, FIG. 5).

Another aspect of the present invention relates to the pharmaceutical composition comprising compound III, IIIa or IIIb or a mixture thereof and hydroxypropyl cellulose and/or croscarmellose sodium.

According to another aspect, the present invention relates to the pharmaceutical composition comprising corn starch and hydroxypropyl cellulose and/or croscarmellose sodium.

According to another aspect, the present invention relates to the pharmaceutical composition comprising lactose monohydrate, hydroxypropyl cellulose, croscarmellose sodium, magnesium stearate and pregelatinized starch or corn starch.

According to another aspect, the present invention relates to a pharmaceutical composition comprising a tablet core consisting of compound III, lactose monohydrate, hydroxypropyl cellulose, croscarmellose sodium, magnesium stearate and pregelatinized starch or corn starch.

According to another aspect, the present invention relates to a pharmaceutical composition comprising a tablet core consisting of 1-30% (wt/wt) compound III, 63-83% (wt/wt) lactose monohydrate, 5-25% (wt/wt) pregelatinized starch, 1-3% (wt/wt) hydroxypropyl cellulose, 1-5% (wt/wt) croscarmellose sodium, and 0.5-3.5% (wt/wt) magnesium stearate.

According to another aspect, the present invention relates to a pharmaceutical composition comprising a tablet core consisting of 8-24% (wt/wt) compound III, 53-70% (wt/wt) lactose monohydrate, 10-20% (wt/wt) pregelatinized starch, 1-3% (wt/wt) hydroxypropyl cellulose, 1-5% (wt/wt) croscarmellose sodium, and 0.5-3.5% (wt/wt) magnesium stearate.

According to another aspect, the present invention relates to a pharmaceutical composition comprising a tablet core consisting of 1-30% (wt/wt) compound III, 50-80% (wt/wt) lactose monohydrate, 5-20% (wt/wt) corn starch, 1-3% (wt/wt) hydroxypropyl cellulose, 1-5% (wt/wt) croscarmellose sodium, and 0.5-3.5% (wt/wt) magnesium stearate.

According to another aspect, the present invention relates to a pharmaceutical composition comprising a tablet core consisting of 8-24% (wt/wt) compound III, 65-75% (wt/wt) lactose monohydrate, 5-20% (wt/wt) corn starch, 1-3% (wt/wt) hydroxypropyl cellulose, 1-5% (wt/wt) croscarmellose sodium, and 0.5-3.5% (wt/wt) magnesium stearate.

Another aspect of the present invention relates to a pharmaceutical composition as defined above for use in the above mentioned diseases, conditions and symptoms.

Another aspect of the present invention relates to a method of treatment of above mentioned diseases, conditions and symptoms.

GENERAL DEFINITIONS

Terms not specifically defined herein should be given the meanings that would be given to them by one skilled in the art in light of the disclosure and the context.

If not otherwise specified, the term compound III relates to the compound of the following structure

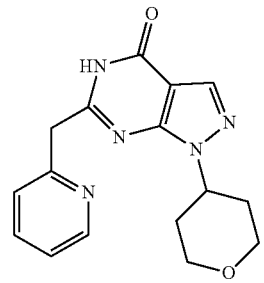 [SMILES: O=c1[nH]c(Cc2ccccn2)nc2c1cnn2C1CCOCC1]

in any polymorphic form or mixtures or pharmaceutically acceptable salts or hydrates thereof.

The term "Subject" means a human patient.

The term "adverse event (AE)" means any untoward medical occurrence, including an exacerbation of a pre-existing condition, in a patient in a clinical investigation who received a pharmaceutical product. The event did not necessarily have to have a causal relationship with this treatment.

The term "adverse event (SAE)" means any AE which resulted in death, was immediately life-threatening, resulted in persistent or significant disability/incapacity, required or prolonged patient hospitalisation, was a congenital anomaly/birth defect, or was to be deemed serious for any other reason if it was an important medical event when based upon appropriate medical judgement which might jeopardise the patient and might require medical or surgical intervention to prevent one of the other outcomes listed in the above definitions.

EXPERIMENTAL PART

List of Abbreviations

AE Adverse Event
BID bis in die (twice daily dosing)
ER emergency room
ESI electrospray ionization
FAS Full Analysis Set HCl hydrochloric acid
HPMC hypromellose=hydroxypropylmethylcellulose
HR high-resolution
IDR intrinsic dissolution rate=intrinsic solubility
i.v. intravenous
M mole, mol/L
MedDRA Medical Dictionary for Drug Regulatory Activities
ml milliliter
MS mass spectrometry
m/z mass-to-charge ratio
NMR nuclear magnetic resonance
PDE phosphodiesterase
qd quaque die (once a day)
rpm revolutions per minute
RT room temperature
SAE Serious Adverse Event
TMS Tetramethylsilane
TS Treated set
wt weight
XRPD X-ray powder diffraction Preparation and Physicochemical Characterization of Compound III Description of Analytical Methods Used

| ESI mass spectrometry (ESI+) | |
|---|---|
| Instrument | QTOF HDMS Synapt (Micromass, Manchester, UK) |
| Instrument control software | Masslynx 4.1 |
| Ion source | ESI + (Lockspray source) |
| Lockspray/DXC | on/off |
| Calibration | sodium formate, Leu-Enkephalin lockmass calibration |
| Resolution MS1(LM/HM) | 4.7/15 |
| Resolving power (FWHM) | 14935 at m/z 312 (W mode) |
| MCP voltage | 1700 V |
| Capillary voltage | +3.0 kV |
| Cone voltage | 8 V |
| Collision energy | 2 eV |
| Collision gas | Argon |
| Source temperature | 120° C. |
| Desolvation temperature | 200° C. |
| Cone gas | nitrogen 48 L/h |
| Desolvation gas | nitrogen 600 L/h |
| Sample inlet | Via UPLC (Waters Acquity System) |
| Spray solvent flow rate | 300 µl/min |
| Sample concentration | 0.5 mg/ml in acetonitrile/water (1:1/v:v), 0.5 µl injected |
| Reagents | 0.1% formic acid in acetonitrile (ULC/MS, Biosolve) 0.1% formic acid in water (ULC/MS, Biosolve) |
| Scan range | 50-1000 u |
| Scan time | 0.16 s |
| No. of scans combined | 15 |
| Data threshold | 2.0% |

| $^1$H NMR spectroscopy | |
|---|---|
| Instrument | Bruker Avance III 600 NMR spectrometer |
| Frequency | 600.38 MHz |
| Software | Bruker TopSpin ® version 3.0 |
| Pulse program | zg30 |
| Solvent | DMSO-d6, Sigma Aldrich, Batch MKBT4612V |
| Concentration | 15.3 mg/0.6 ml |
| Temperature | 27° C. |
| Calibration | Tetramethylsilane (=TMS: δ = 0.00 ppm) |
| Sweep width | 12315 Hz |
| Size | 64K data points |
| Pulse width | 30 degree |
| Relaxation delay | 2 s |
| Number of scans | 64 |
| Dummy scans | 2 |
| Apodization | zerofilling to 128K data points exponential multiplication (LB: 1.00 Hz) |

| $^{13}$C NMR spectroscopy | |
|---|---|
| Instrument | Bruker Avance III 600 NMR spectrometer |
| Frequency | 150.98 MHz |
| Software | Bruker TopSpin ® version 3.0 |
| Pulse program | zgpg30 |
| Solvent | DMSO-d6, Sigma Aldrich, Batch MKBT4612V |
| Concentration | 15.3 mg/0.6 ml |
| Temperature | 27° C. |
| Calibration | Unified scale (IUPAC Recommendations 2001) |
| Sweep width | 37879 Hz |
| Size | 64K data points |
| Pulse width | 30 degree |
| Relaxation delay | 10 s |
| Number of scans | 3072 |
| Dummy scans | 4 |
| Apodization | zerofilling to 128K data points Exponential multiplication (LB: 1.00 Hz) |

X-Ray Powder (XRPD) Diagram

X-ray powder diagrams were generated using a STOE-STADI P-diffractometer in transmission mode fitted with a MYTHEN-detector and a Cu-anode as X-ray source with monochromatic CuKα1 radiation (λ=1.54056 Å, 40 kV, 40 mA). The standard error range for the 2-theta values is ±0.2°.

RAMAN Spectroscopy

Kaiser Optics RXN2 dispersive Raman PhAT Probe with 6 mm optics, laser power 400 mW, Exposure time 1 sec. The spectral resolution is 4 $cm^{-1}$.

Preparation of Compound III a) Preparation of Compound IIIa (Crude, Form a):

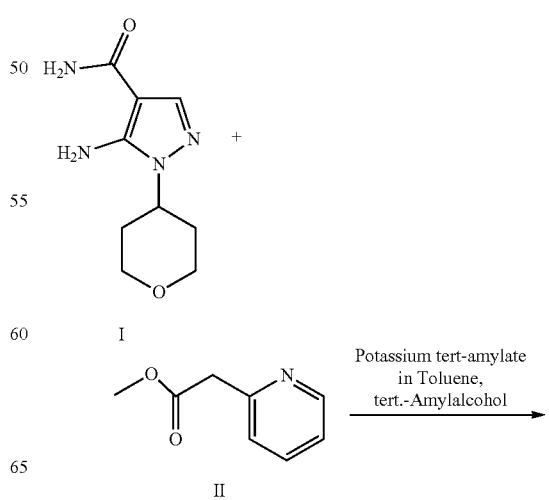

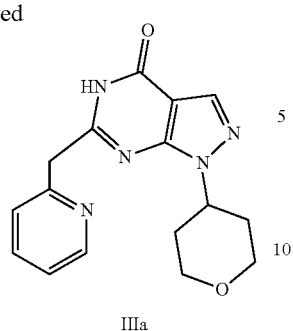

IIIa

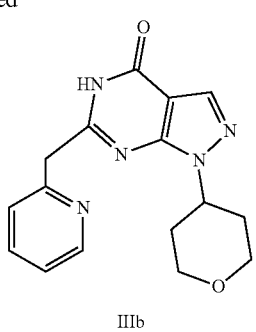

IIIb

5-Amino-1H-pyrazole-4-carboxylic acid amide I (64.0 kg, 304.4 mol) and 2-pyridineacetic acid methyl ester II (69.1 kg, 457.1 mol) are suspended in tert.-Amyl alcohol (84 kg) and heated to 80-90° C. A solution of potassium tert.-amylate (25% in toluene, 230.6 kg, 457.1 mol) is added at 80-90° C. The dropping funnel is rinsed with toluene (84 kg). The reaction mixture is heated to reflux. After complete conversion the mixture is cooled down to 55-65° C. and water (192 kg) is added to the reaction mixture. After phase separation ethanol (38.0 kg) and acetic acid (11.0 kg) is added to the aqueous phase at 55-65° C. A second portion of acetic acid (11.0 kg) is added at 55-65° C. The dropping funnel is rinsed with ethanol (25 kg) and the reaction mixture is cooled to 15-25° C. The suspension is filtered and the filter cake washed with water (256 kg). The isolated material is dried at max. 60° C. to give Compound IIIa (crude, form a) (75.8-85.3 kg, 80-90%).

Optionally, crystallization can be initiated by seeding with compound IIIa prior to addition of the second portion acetic acid.

NMR ($^1$H, 600 MHz, DMSO-d$_6$): 12.26 (1H, s), 8.48 (1H, br. d), 8.05 (1H, s), 7.77 (1H, tb), 7.41 (1H, d), 7.28 (1H, dd), 4.75 (1H, m), 4.20 (2H, s), 3.94 (2H, m), 3.49 (2H, m), 2.09 (2H, m), 1.80 (2H, m).

NMR ($^{13}$C, 150 MHz, DMSO-d$_6$): 158.4, 158.3, 156.7, 152.0, 149.6, 137.4, 134.5, 124.0, 122.6, 104.7, 66.4, 53.3, 43.3, 32.4.

HRMS (ESI): m/z 312 ([M+H]$^+$; 312.1465).

See Table 1 and FIG. 1 for characterizing data.

b) Preparation of Compound IIIb (Crude, Form b):

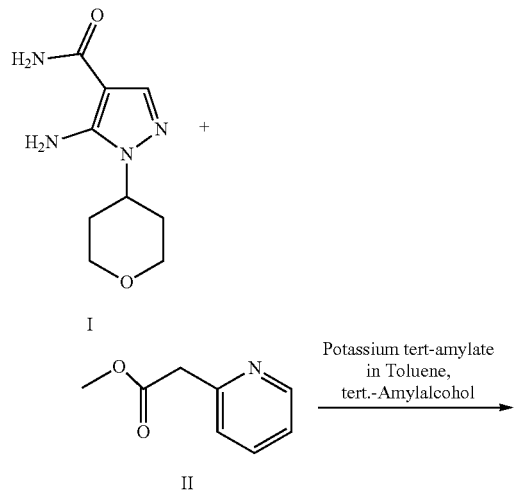

I

II

Potassium tert-amylate in Toluene, tert.-Amylalcohol →

5-Amino-1H-pyrazole-4-carboxylic acid amide I (50.0 kg, 237.8 mol) and 2-pyridineacetic acid methyl ester II (53.9 kg, 356.6 mol) are suspended in tert.-Amyl alcohol (65.6 kg) and heated to 80-90° C. A solution of potassium tert.-amylate (25% in toluene, 180.2 kg, 356.6 mol) is added at 80-90° C. The dropping funnel is rinsed with toluene (43.5 kg). The reaction mixture is heated to reflux. After complete conversion the mixture is cooled down to 55-65° C. and water (150 kg) is added to the reaction mixture. The mixture is cooled down to 15-25° C. After phase separation ethanol (23.7 kg) and acetic acid (17.2 kg) is added to the aqueous phase at 15-30° C. The suspension is stirred for 60 min at 15-25° C. The suspension is filtered and the filter cake washed with water (200 kg). The isolated material is dried at max. 60° C. to give Compound IIIb (crude, form b) (51.8-59.2 kg, 70-80%).

NMR ($^1$H, 600 MHz, DMSO-d$_6$): 12.26 (1H, s), 8.48 (1H, br. d), 8.05 (1H, s), 7.77 (1H, tb), 7.41 (1H, d), 7.28 (1H, dd), 4.75 (1H, m), 4.20 (2H, s), 3.94 (2H, m), 3.49 (2H, m), 2.09 (2H, m), 1.80 (2H, m).

NMR ($^{13}$C, 150 MHz, DMSO-d$_6$): 158.4, 158.3, 156.7, 152.0, 149.6, 137.4, 134.5, 124.0, 122.6, 104.7, 66.4, 53.3, 43.3, 32.4.

HRMS (ESI): m/z 312 ([M+H]$^+$; 312.1465).

Figure 2:
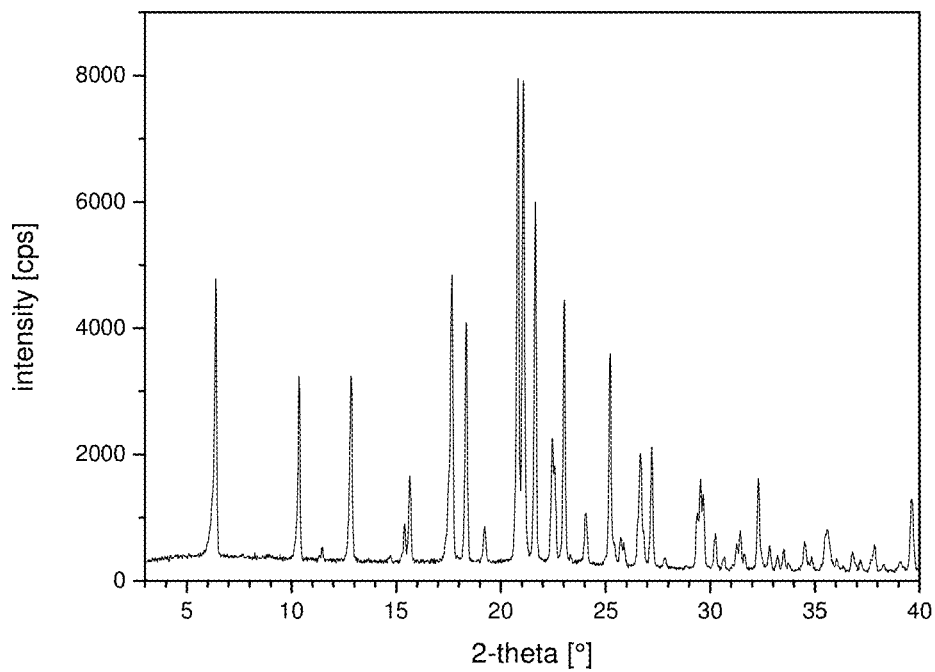
FIG. 2 shows the X-ray powder diffraction pattern of Compound IIIb.

See Table 2 and FIG. 2 for characterizing data.

c) Preparation of Compound IIIa (Unmilled, Form a) Via Recrystallization

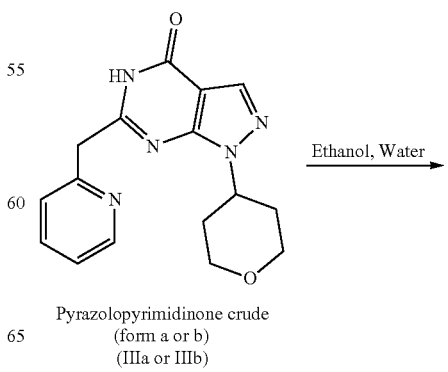

Pyrazolopyrimidinone crude
(form a or b)
(IIIa or IIIb)

Ethanol, Water →

-continued

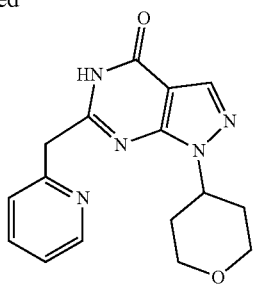

Pyrazolopyrimidinone unmilled
(form a)
(IIIa)

Compound IIIa or IIIb (crude, form a or form b) (44.5 kg, 142.9 mol) is suspended in ethanol (474 kg) and water (13.4 kg). The mixture is heated to reflux and stirred for 45 min. The solution is cooled to 72-78° C. and polish filtered. The filter is rinsed with ethanol (54 kg). The mixture is cooled to 58-65° C. Optionally, crystallization can be initiated by seeding with compound IIIa (form a) after cooling to 58-65° C. The mixture is cooled to 0-10° C. The suspension is filtered and the filter cake washed with ethanol (70 kg). The isolated material is dried at max. 60° C. to give Compound IIIa (unmilled, form a) (37.8-42.3 kg, 85-95%).

NMR ($^1$H, 600 MHz, DMSO-$d_6$): 12.26 (1H, s), 8.48 (1H, br. d), 8.05 (1H, s), 7.77 (1H, tb), 7.41 (1H, d), 7.28 (1H, dd), 4.75 (1H, m), 4.20 (2H, s), 3.94 (2H, m), 3.49 (2H, m), 2.09 (2H, m), 1.80 (2H, m).

NMR ($^{13}$C, 150 MHz, DMSO-$d_6$): 158.4, 158.3, 156.7, 152.0, 149.6, 137.4, 134.5, 124.0, 122.6, 104.7, 66.4, 53.3, 43.3, 32.4.

HRMS (ESI): m/z 312 ([M+H]$^+$; 312.1465).

See Table 1 and FIG. 1 for characterizing data.

d) Preparation of Compound IIIb (Unmilled Form b) Via Recrystallization

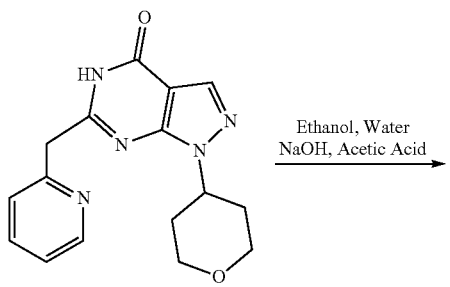

Pyrazolopyrimidinone crude
(form a or b)
(IIIa or IIIb)

Ethanol, Water
NaOH, Acetic Acid
→

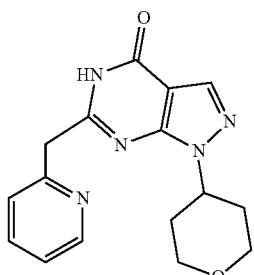

Pyrazolopyrimidinone unmilled
(form b)
(IIIb)

Compound IIIa or IIIb (crude, form a or form b) (2.2 kg, 7.1 mol) is suspended in ethanol (4.4 L) and water (7.7 L) at room temperature. Aqueous sodium hydroxide (45%, 691 g, 7.7 mol) is added via a pump keeping the internal temperature at 15-25° C. The pump is rinsed with water (1.1 L) and the reaction mixture stirred at room temperature for 35 min. Acetic acid (515 g, 8.4 mol) is added via a pump keeping the internal temperature at 15-25° C. The pump is rinsed with ethanol (1.1 L) and the reaction mixture stirred at room temperature for 75 min. The suspension is filtered and the filter cake washed with water (8.8 kg). The isolated material is dried at max. 60° C. to give Compound IIIb (unmilled, form b) (2.0 kg, 92%).

NMR ($^1$H, 600 MHz, DMSO-$d_6$): 12.26 (1H, s), 8.48 (1H, br. d), 8.05 (1H, s), 7.77 (1H, tb), 7.41 (1H, d), 7.28 (1H, dd), 4.75 (1H, m), 4.20 (2H, s), 3.94 (2H, m), 3.49 (2H, m), 2.09 (2H, m), 1.80 (2H, m).

NMR ($^{13}$C, 150 MHz, DMSO-$d_6$): 158.4, 158.3, 156.7, 152.0, 149.6, 137.4, 134.5, 124.0, 122.6, 104.7, 66.4, 53.3, 43.3, 32.4.

HRMS (ESI): m/z 312 ([M+H]$^+$; 312.1465).

See Table 2 and FIG. 2 for characterizing data.

e) Micronization Process Compound IIIa

The micronization was performed using the pilot plant opposed jet mill 140 AFG (Hosokawa-Alpine AG, Augsburg) applying the following process parameters for Compound IIIa (unmilled, form a):

| Milling Pressure [bar] | Classifier Speed [rpm] | Dosage [kg/h] | Injector pressure [bar] |
|---|---|---|---|
| 5.0 | 3500 | 15.0 | 1 |

A particle size distribution in terms of x90 <28 μm was achieved. For analysis laser diffraction/dry dispersion Sympatec was used.

Solid State Properties of Compound III Crude (Form a or b) and Compound III Unmilled (Form a or b), Respectively Appearance In the solid state, the Compounds IIIa and IIIb are white microcrystalline materials.

Crystallinity and Polymorphism

Figure 3:
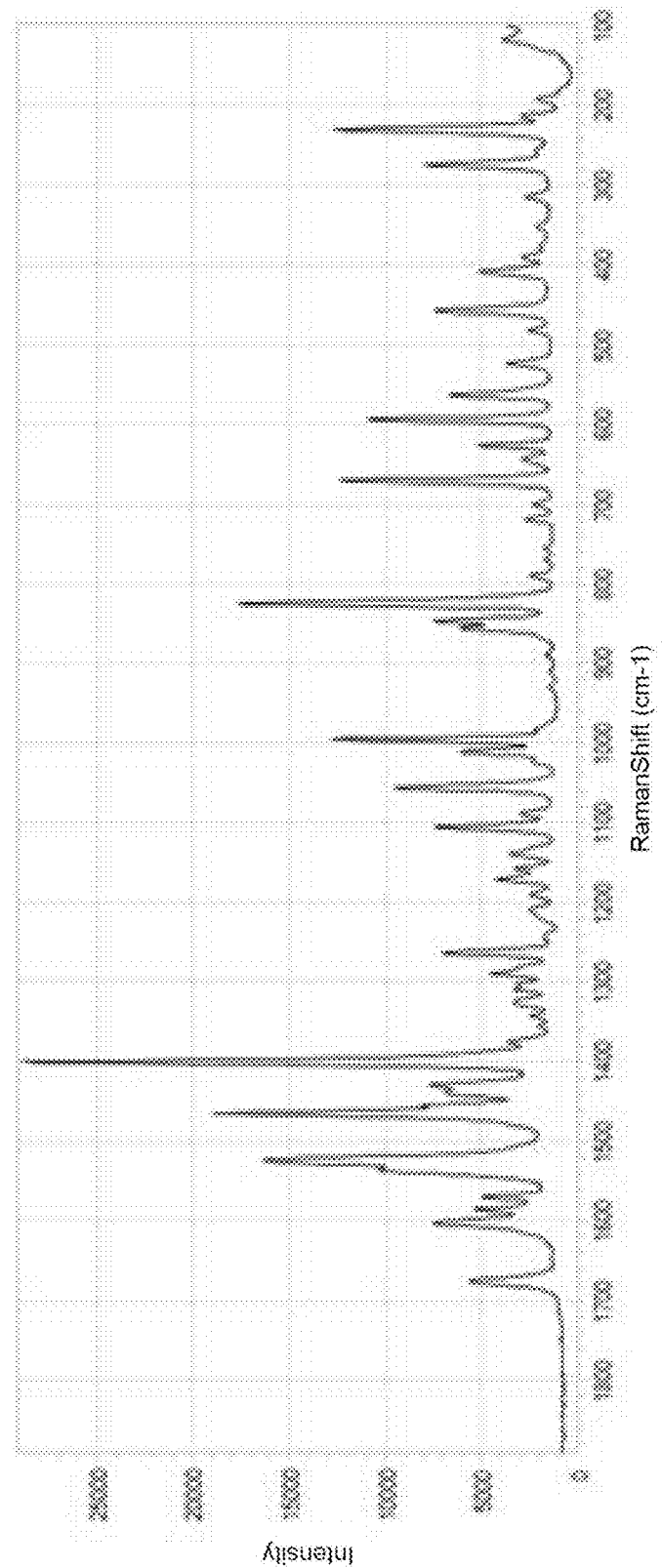
FIG. 3 shows the Raman spectrum of Compound IIIa.

Compound IIIa is highly crystalline as can be seen in the X-ray powder diffraction diagram in FIG. 1 and RAMAN spectrum in FIG. 3.

The X-ray powder reflection and intensities (standardised) are shown in Table 1.

TABLE 1

| 2 Θ [°] | d-value [Å] | intensity I/I$_0$ [%] |
|---|---|---|
| 7.66 | 11.54 | 28 |
| 8.96 | 9.86 | 52 |
| 10.39 | 8.50 | 34 |
| 13.06 | 6.78 | 13 |
| 14.27 | 6.20 | 6 |
| 14.70 | 6.02 | 38 |
| 15.22 | 5.82 | 12 |
| 15.35 | 5.77 | 6 |
| 16.40 | 5.40 | 6 |
| 17.33 | 5.11 | 100 |
| 17.89 | 4.95 | 43 |
| 18.89 | 4.70 | 17 |
| 19.14 | 4.63 | 28 |
| 19.50 | 4.54 | 6 |
| 20.26 | 4.38 | 6 |
| 20.89 | 4.25 | 63 |

TABLE 1-continued

| 2 Θ [°] | d-value [Å] | intensity I/I₀ [%] |
|---|---|---|
| 21.25 | 4.18 | 76 |
| 22.33 | 3.98 | 7 |
| 22.85 | 3.89 | 53 |
| 23.31 | 3.81 | 62 |
| 23.75 | 3.74 | 37 |
| 24.05 | 3.70 | 14 |
| 24.97 | 3.56 | 45 |
| 25.97 | 3.43 | 10 |
| 26.30 | 3.39 | 8 |
| 26.44 | 3.37 | 8 |
| 26.95 | 3.31 | 23 |
| 27.09 | 3.29 | 25 |
| 27.35 | 3.26 | 10 |
| 28.04 | 3.18 | 6 |

In Table 1 above the value "2-theta [°]" denotes the angle of diffraction in degrees and the d-value [Å] denotes the specified distances in Å between the lattice planes.

The crystalline Compound IIIa is characterised in that in the x-ray powder diagram has, inter alia, the characteristic values 2-theta=17.3°±0.2° (100% relative intensity), 21.3°±0.2° (76% relative intensity), 20.9°±0.2° (63% relative intensity), 23.3°±0.2° (62% relative intensity), 22.9°±0.2° (53% relative intensity), 9.0°±0.2° (52% relative intensity), 25.0°±0.2° (45% relative intensity), 17.9°±0.2° (43% relative intensity), 14.7°±0.2° (38% relative intensity), 23.8°±0.2° (37% relative intensity), 10.4°±0.2° (34% relative intensity), 7.7°±0.2° (28% relative intensity), 19.1°±0.2° (28% relative intensity), 27.1°±0.2° (25% relative intensity), 27.0°±0.2° (23% relative intensity) (most prominent peaks in the diagram of FIG. 1, Table 1).

Compound IIIa is characterised in that in the x-ray powder diagram has strong unique reflections at the values 2-theta=7.7°±0.2°, 9.0°±0.2°.

The ratio of a mixture containing compound IIIa (crude, form a) and a certain amount of compound IIIb (crude, form b) did not change after storage under ambient conditions for 28 months.

RAMAN spectrum (characteristic bands) [cm⁻¹]: 1190±2, 1401±2 and 1675±2.

Figure 4:
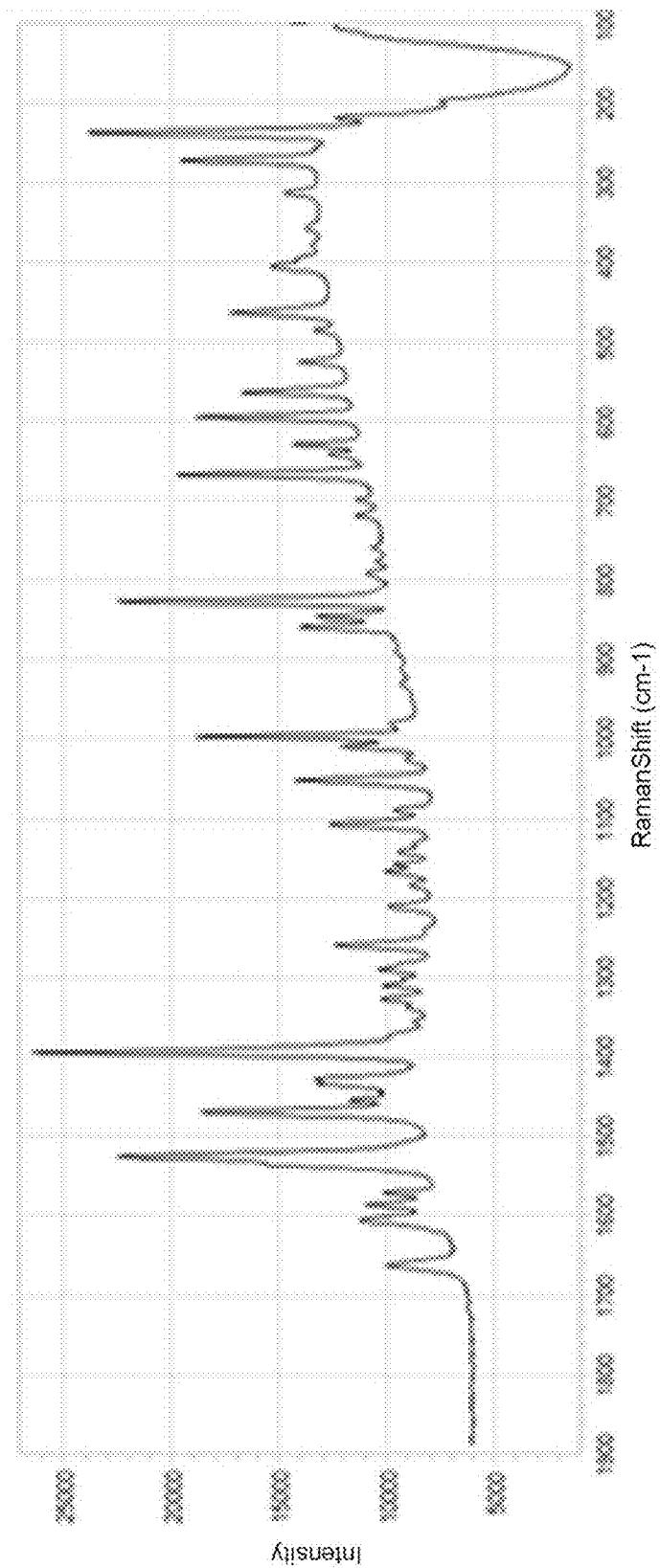
FIG. 4 shows the Raman spectrum of Compound IIIb.

Compound IIIb is highly crystalline as can be seen in the X-ray powder diffraction diagram in FIG. 2 and RAMAN spectrum in FIG. 4.

The X-ray powder reflection and intensities (standardised) are shown in Table 2.

TABLE 2

| 2 Θ [°] | d-value [Å] | intensity I/I₀ [%] |
|---|---|---|
| 6.38 | 13.84 | 60 |
| 10.36 | 8.53 | 41 |
| 11.45 | 7.72 | 6 |
| 12.85 | 6.88 | 41 |
| 14.71 | 6.02 | 5 |
| 15.40 | 5.75 | 11 |
| 15.66 | 5.66 | 21 |
| 17.65 | 5.02 | 61 |
| 18.35 | 4.83 | 52 |
| 19.22 | 4.61 | 11 |
| 20.81 | 4.26 | 100 |
| 21.08 | 4.21 | 99 |
| 21.64 | 4.10 | 76 |
| 22.46 | 3.96 | 29 |
| 22.54 | 3.94 | 24 |
| 23.03 | 3.86 | 57 |
| 24.05 | 3.70 | 14 |

TABLE 2-continued

| 2 Θ [°] | d-value [Å] | intensity I/I₀ [%] |
|---|---|---|
| 25.21 | 3.53 | 45 |
| 25.73 | 3.46 | 9 |
| 25.87 | 3.44 | 7 |
| 26.67 | 3.34 | 25 |
| 27.20 | 3.28 | 27 |
| 27.83 | 3.20 | 4 |
| 29.38 | 3.04 | 14 |
| 29.53 | 3.02 | 20 |
| 30.24 | 2.95 | 9 |

In Table 2 above the value "2-theta [°]" denotes the angle of diffraction in degrees and the d-value [Å] denotes the specified distances in Å between the lattice planes.

Compound IIIb is characterised in that in the x-ray powder diagram has, inter alia, the characteristic values 2-theta=20.8°±0.2° (100% relative intensity), 21.1°±0.2° (99% relative intensity), 21.6°±0.2° (76% relative intensity), 6.4°±0.2° (60% relative intensity), 23.0°±0.2° (57% relative intensity), 25.2°±0.2° (45% relative intensity), 10.4°±0.2° (41% relative intensity), 12.9°±0.2° (41% relative intensity), 22.5°±0.2° (29% relative intensity), 27.2°±0.2° (27% relative intensity), 26.7°±0.2° (25% relative intensity) (most prominent peaks in the diagram of FIG. 2, Table 2).

Compound IIIb is characterised in that in the x-ray powder diagram has a strong unique reflection at the value 2-theta=6.4°±0.2°.

RAMAN spectrum (characteristic bands) [cm⁻¹]: 1182±2, 1394±2 and 1663±2.

Examples for Pharmaceutical Composition

The pharmaceutical composition according to the invention is a tablet for oral administration comprising a core, containing compound III, IIIa or IIIb or a mixture thereof and hydroxypropyl cellulose and/or croscarmellose sodium, and further comprising a film coating, enveloping said core.

Examples for Formulation 1

TABLE 3

Composition of tablet core formulation 1

| | Dose strength | | |
|---|---|---|---|
| | 10 mg | 25 mg | 50 mg |
| | Drug load (%, wt/wt) | | |
| | 16 | 8 | 16 |
| Ingredient | [mg/tab] | [mg/tab] | [mg/tab] |
| compound III (Jet milled) | 10.000 | 25.000 | 50.000 |
| Lactose monohydrate | 36.875 | 209.375 | 184.375 |
| Pregelatinized starch | 12.500 | 62.500 | 62.500 |
| Hydroxypropyl cellulose | 1.250 | 6.250 | 6.250 |
| Croscarmellose sodium | 1.250 | 6.250 | 6.250 |
| Magnesium stearate | 0.625 | 3.125 | 3.125 |
| Sub-total: Core tablet | 62.500 | 312.500 | 312.500 |

TABLE 4

Composition of film coated tablets formulation 1

| | Dose strength | | |
| --- | --- | --- | --- |
| | 10 mg [mg/tab] | 25 mg [mg/tab] | 50 mg [mg/tab] |
| Core tablet | 62.500 | 312.500 | 312.500 |
| Film-coat* | 2.500 | 7.500 | 7.500 |
| Total Film-coated tablet | 65.000 | 320.000 | 320.000 |

*Based on the intended color, the film coat consists of different, and commonly used amounts of hypromellose, propylene glycol, talc, titanium dioxide, and iron oxides.

Examples for Formulation 2 (Shown in Table 5 and Table 6)

TABLE 5

Composition of tablet core of formulation 2

| | Dose strength | | | |
| --- | --- | --- | --- | --- |
| | 10 mg | 25 mg | 50 mg | all |
| | Drug load (%, wt/wt) | | | |
| Ingredient | 11.76 [mg/tab] | 11.76 [mg/tab] | 11.76 [mg/tab] | 11.76 [%, wt/wt] |
| compound III (Jet milled) | 10.000 | 25.000 | 50.000 | 11.76 |
| Lactose monohydrate | 62.250 | 155.625 | 311.250 | 73.24 |
| Corn starch | 8.500 | 21.250 | 42.500 | 10.00 |
| Hydroxypropyl cellulose | 1.700 | 4.250 | 8.500 | 2.00 |
| Croscarmellose sodium | 1.700 | 4.250 | 8.500 | 2.00 |
| Magnesium stearate | 0.850 | 2.125 | 4.250 | 1.00 |
| Sub-total Core | 85.000 | 212.5 | 425.000 | 100.00 |

TABLE 6

Composition of film coated tablets formulation 2

| | Dose strength | | |
| --- | --- | --- | --- |
| | 10 mg [mg/tab] | 25 mg [mg/tab] | 50 mg [mg/tab] |
| Core tablet | 85.000 | 212.5 | 425.000 |
| Film-coat* | 3.000 | 5.500 | 9.000 |
| Total Film coated tablet | 88.000 | 218.000 | 434.000 |

*Based on the intended color, the film coat consists of different, and commonly used amounts of hypromellose, propylene glycol, talc, titanium dioxide, and iron oxides.

As one example for the fast and complete dissolution characteristics of the formulations described, the dissolution profiles of core tablets and film-coated tablets 50 mg (compare Table 5 and Table 6) are shown in FIG. 5.

A pharmaceutical composition comprising compound III, IIIa or IIIb or a mixture thereof in combination with hydroxypropyl cellulose and/or croscarmellose sodium leads to adjustment of the drug load to the same level for all dose strengths, and a fast dissolution of the tablet can be reached irrespective of the low intrinsic dissolution rate of compound III in the physiologically relevant pH range above pH 4.

This results in a more flexible usage of the granules, as they can be compressed to all dose strengths at adequate tablet size and tablet weight. A coloured film coat can be added that allows differentiation of the different dosage strengths.

Formulation 1 and formulation 2 can be obtained by using either compound IIIa or compound IIIb or mixtures thereof, respectively.

Manufacturing of Film-Coated Tablets:

A) Material Used

TABLE 7

Description of needed excipient grades

| Ingredient | Particular preferred grade/type (in addition to pharmacopoeial USP/NF, Ph.Eur., JP specification) |
| --- | --- |
| Lactose monohydrate | crystalline, fine |
| Corn starch | no additional specification |
| Pregelatinized starch | no additional specification |
| Hydroxypropyl cellulose | no additional specification |
| Croscarmellose sodium | no additional specification |
| Magnesium stearate | Specific surface area about 2-10 m$^2$/g |

B) Equipment Used

The following equipment was used in the process of preparing the pharmaceutical composition according to the invention.

The formulation 1 is preferably produced using the following equipment:

Mixing vessel with propeller mixer for granulation liquid;
High shear mixer/granulator (e.g. different scales of Glatt VG or Diosna type)+Wet screen machine (e.g. Alexanderwerk)+Fluid-bed dryer (e.g. different scales of Glatt GPCG or Glatt WSG type);
Dry screen machine (e.g. Quadro Comil);
Free fall blender (e.g. Servolift or container mixer); single punch or Rotary tablet press (e.g. from supplier Fette, or Korsch, or Kilian);
Mixing vessel with propeller mixer and/or homogenizer for film coating suspension;
Film coater (i.e. film coater with perforated coating drum)

The formulation 2 is preferably produced using the following equipment:

Mixing vessel with propeller mixer for granulation liquid;
Fluidized-bed granulator/dryer (e.g. different scales of Glatt GPCG or Glatt WSG type)
Dry screen machine (e.g. Quadro Comil);
Free fall blender (e.g. Servolift or container mixer); single punch or Rotary tablet press (e.g. from supplier Fette, or Korsch, or Kilian);
Mixing vessel with propeller mixer and/or homogenizer for film coating suspension;
Film coater (i.e. film coater with perforated coating drum)

C) Process Description:

Granulation Liquid

As a first step the granulation liquid for the wet granulation process is prepared.

Purified water of about 10-90° C. is filled into a suitable mixing vessel. Then a binding agent such as hydroxypropyl cellulose or hypromellose is stirred in, and the dispersion is cooled down if necessary to room temperature. If necessary, the liquid is allowed to stand overnight (completeness of solution/degassing) and stirred up before use. If necessary, any weight loss is compensated with purified water. The dry matter (solid content) of this granulation liquid is preferably in the range of 4-7% (wt/wt, assuming feasibility for a range of 2-10%, wt/wt).

Both formulations 1 and 2 may be produced by high shear or fluid bed granulation. For each formulation the preferred production process is described below, but the production of each formulation using either equipment leads to reasonable drug product. The selection of the granulation process depends on available equipment and on economic decisions.

High Shear Granulation Process
(Preferably for Production of Formulation 1)

For high shear granulation the required quantity of compound III active ingredient (depending on the dose strength), lactose monohydrate, corn starch or pregelatinized starch, and mannitol (optionally) are filled in the product bowl of a high-shear mixer/granulator, then mixed homogeneously for about 3-4 min using impeller and chopper blades. Next, the granulation liquid is added either manually or by spray nozzles and the wet mass is granulated for about 2-3 min, again using impeller and chopper blades. After discharging of the high shear mixer/granulator the wet granules are wet-screened through a 3.0 mm mesh size sieve to destroy large agglomerates.

The wet-screened material is transferred to a conventional fluid bed drier (or alternatively to a tray drier) and dried at an inlet air temperature of approximately 60-90° C. Granules are dried when the water activity of the resulting dry granules is below 0.6. The dried granules are then dry screened with the help of a Comil screen machine, The screened granules are filled into a suitable free-fall blender, e.g. a container mixer, croscarmellose sodium (crosslinked carboxymethylcellulose sodium) and MgStearate are added subsequently, and blended for in sum 10-20 min, preferably 15 minutes at a mixing speed of 10 rpm until homogeneous.

Fluid Bed Granulation Process
(Preferably for Production of Formulation 2)

For the fluidised bed wet granulation process the required quantity of compound III active ingredient (depending on the dose strength and formulation variant), lactose monohydrate, corn starch or pregelatinized starch, and mannitol (optionally) are filled in the product bowl of a fluid-bed granulator, then mixed homogeneously in the chamber of the fluid-bed granulator. Next, the granulation liquid is added by spraying for granulation in the chamber of the fluid-bed granulator at an inlet air temperature of approximately 60-90° C., preferably 75-85° C. until the target amount of granulation liquid is sprayed. After finishing the granulation step, the granules are dried in the same chamber at an inlet air temperature of approximately 60-90° C. Granules are dried when the water activity of the resulting dry granules is below 0.6, while the compression properties of these granules are improved by lower moisture contents. The dried granules are then dry-screened using a Comil screening machine. The screened granules are filled into a suitable free-fall blender, e.g. a container mixer. Croscarmellose sodium (crosslinked carboxymethylcellulose sodium) and Magnesium stearate are added either together or subsequently, and blended either together, or subsequently, for in sum 10-60 min, preferably 15 minutes at a mixing speed of 10 rpm until homogeneous.

Compression

The final tableting blend is compressed on a suitable tablet press (e.g. rotary press) to the respective target weight of the required dose strength of compound III tablets using the appropriate tools (e.g. in case of 10 mg tablets: 6 mm round; biconvex; with bevelled edges, or 5.5 mm round; biconvex; with bevelled edges, in case of 25 mg tablets: 8 mm round; biconvex; with bevelled edges or 12×5.9 mm oblong shaped, in case of 50 mg tablets: 14×6.8 mm oblong shaped or 12×5.9 mm oblong shaped). Predetermined hardness specifications for the different tool dimensions have to be followed in order to achieve the intended drug dissolution profile and product characteristics. Tablets of all dosages are compressed to result in a tensile strength of approximately 1.5 MPa, this tensile strength is translated into individual hardness specifications for all dosages according to the equations given in the USP/NF.

Film Coating

A colored film coating has to be applied to the tablet cores in order to achieve a stable and consumer friendly product, especially for product differentiation to prevent from medication errors. For this purpose a coating suspension is prepared by filling purified water into a suitable mixing vessel, and dissolving propyleneglycol and then hydroxypropylmethylcellulose with the help of a propeller or high shear stirrer. In a next step an aqueous slurry of titanium dioxide, talc, iron oxide yellow and/or iron oxide red if needed (in case of coloured film tablets) is poured and stirred into the film-forming polymer solution. The dry matter of this coating suspension is in the range of 10-15%, preferably about 12-13%. The suspension may also be prepared from a ready to use dry mixture that contains the same or chemically comparable components.

The above prepared tablet cores are filled into a suitable film coater (i.e. with perforated pan and top spray system, alternatively Accela Cota with a 36" pan with perforated pan and top spray system is also applicable, less preferred is a pan coater), and preheated up to a temperature of approximately 40-50° C. or above at an inlet air temperature of approximately 60-70° C., preferably at 65° C. After this product temperature is reached the coating suspension is sprayed onto the cores with the help of one or more spray nozzles at a spray pressure of about 1-5 bar depending on nozzle design, production scale and spray rate. A spray rate of about 20-600 g/min (depending on the batch size as well as drum speed and other operating conditions) at an inlet air temperature of about 40-80° C., preferably 60° C. It is important to control and maintain the product temperature during spraying at a level of between 40-50° C. to achieve a high quality film-coat. After the spraying is finished the film-coated tablets may be dried if needed, then cooled down to 40° C. or below, preferably to approx. 30° C. before the equipment is discharged. The total process time for the film-coating is in the range of 1-4 hours (depending on the spray rate as well as the batch size), other process durations are also feasible.

The film-coated tablets of formulations 1 and 2, respectively, release the compound III active ingredient rapidly and in a largely pH-independent fashion, with complete release occurring within less than 60 min and release of the major fraction (more than 80%) occurring within less than 45 min. In accordance with the present invention, an increased dissolution rate of the active ingredient (FIG. 5) is achieved. At least or more than 80% of the drug load is dissolved typically after 45 min, more typically after 30 min, and most typically after 15 min using the paddle method (according to USP/NF and Ph. Eur. apparatus 2) dissolution test conditions at 50 rpm and at pH 6.8 (900 mL of 0.05 M Phosphate buffer (FIG. 5).

Based on the quality of the tablets produced by the industrial process, the use of compound IIIa for the manufacture of formulation 2 is preferred.

Formulation 1 and formulation 2 are both useful pharmaceutical compositions.

CLINICAL TRIALS

Prevention of Disease Relapse: Study Design, Inclusion Criteria of Patients, Statistical Method Regarding reducing the exacerbations of symptoms characterizing relapse, including suicidality, the clinical trial disclosed below was designed to show the efficacy of compound III in improvement of cognitive impairment in patients with schizophrenia as compared to placebo. All patients were on stable antipsychotic treatment (see Table 8 in FIGS. 6A-6C). The study was a multinational, multicentre, randomised, double-blind, placebo-controlled, parallel group trial.

STUDY Medicine

Compound III (10, 25 and 50 mg) and matching placebo were supplied as film-coated tablets (formulation 1).

Study Population

In total, 516 patients with schizophrenia on stable antipsychotic treatment (Table 8 in FIGS. 6A-6C) as described below were randomized into this trial.

Inclusion Criteria

Patients with established diagnoses of schizophrenia (per Diagnostic and Statistical Manual of Mental Disorders, Fifth Edition (DSM-V) with the following clinical features:
1) Clinically stable and are in the residual (non-acute) phase of their illness for at least 8 weeks
2) Current antipsychotic and concomitant psychotropic medications must meet the criteria below:
   a) Maintained on current atypical (second generation) antipsychotic medications (in any approved dosage form)
   b) and on current dose for at least 8 weeks prior to randomisation, and/or
   c) Maintained on current typical (first generation) antipsychotic medications and on current dose for at least 6 months, optionally combined with anticholinergics if treated with a stable dose for at least 6 months prior to randomisation, and/or
   d) Maintained on current concomitant psychotropic medications other than anticholinergics, antiepileptics and lithium, and on current dose for at least 8 weeks prior to randomisation. Antiepileptics and lithium are allowed if initiated at least 6 months prior to randomisation.
3) Have no more than a "moderate" severity rating on hallucinations and delusions (Positive and Negative Syndrome Scale (PANSS)-positive syndrome Hallucinatory Behavior item score 4 and Delusions item score ≤4)
4) Have no more than a "moderate" severity rating on positive formal thought disorder (PANSS-positive syndrome Conceptual Disorganization item score ≤4)
5) Have a minimal level of extrapyramidal symptoms (Simpson-Angus Scale total score <6) and depressive symptoms (PANSS-general psychopathology syndrome Depression item score ≤4)

Exclusion Criteria
1) Patient treated with more than two antipsychotic medications (including more than two dosage forms)
2) Any suicidal behavior in the past 2 years (i.e. actual attempt, interrupted attempt, aborted attempt, or preparatory acts or behavior)
3) Any suicidal ideation of type 4 or 5 in the Columbia Suicidal Severity Rating Scale (C-SSRS) in the past 3 months (i.e. active suicidal thought with intent but without specific plan, or active suicidal thought with plan and intent)
4) History or diagnosis of symptomatic and unstable/uncontrolled gastrointestinal, hepatic, renal, respiratory, cardiovascular, metabolic, immunological, haematological or hormonal disorders
5) Diseases of the central nervous system (including but not limited to any kind of seizures, stroke or any psychiatric disorders other than schizophrenia)

Randomization

Patients eligible for the trial based on the aforementioned criteria were assigned at random in a 2:1:1:1:1 ratio to one of 5 study arms (placebo qd, 10 mg qd, 25 mg qd, 50 mg qd, and 100 mg qd) and followed for 12 weeks of treatment.

Variables Assessed

The results of the primary and key secondary efficacy endpoints and the primary and secondary safety endpoints are summarized below.

Efficacy Endpoints

The primary endpoint in this trial is the change from baseline in cognitive function as measured by the Measurement and Treatment research to Improve Cognition in Schizophrenia (MATRICS) Consensus Cognitive Battery (MCCB) composite score after 12 weeks of treatment. The key secondary efficacy endpoint is the change from baseline in everyday functional capacity as measured by Schizophrenia Cognition Rating Scale (SCoRS) global ratings after 12 weeks of treatment.

Safety Endpoints

The primary safety endpoints are as follows:
  Occurrence of adverse events (AEs)/serious adverse events (including the abnormalities of physical examination, vital signs, electrocardiogram test and laboratory tests)
  Occurrence of protocol-specified adverse events of special interest
  Dramatic worsening of disease state as assessed by PANSS
  Suicidality as assessed by Columbia Suicidal Severity Rating Scale (C-SSRS)

The secondary safety endpoint is the change in psychopathology symptoms as assessed by PANSS.

Statistical Methods

The statistical analysis was performed in a two-stage fashion. Stage 1 analysis was performed after 70% of patients complete the 12-week treatment period, and 30% of patients were randomly selected from the 70% of patients for Stage 1 analysis. Stage 1 analysis was considered as an internal-pilot study with the objective to explore the Cambridge Neuropsychological Test Automated Battery (CANTAB) endpoints, while Stage 2 was considered as the confirmatory stage to formally test the primary endpoint selected from Stage 1. No adaptation in trial conduct was made, and only the statistical analysis plan was different for the two stages. This report summarizes the results of the Stage 2 analysis.

Two analysis sets were used. The treated set (TS) consisted of all patients who were randomised and treated with at least one dose of study drug; this set was used for the analysis of safety results. The full analysis set (FAS) consisted of all randomisation patients who were treated with at least one dose of study drug and had a baseline and at least one post-baseline on-treatment efficacy measurement (MCCB or CANTAB) measurement. The FAS was used for the primary analyses in both stages. For the Stage 1 analysis, only patients who met the FAS definition were included and from those patients, 120 were randomly selected based on the pre-defined number of patients for each group.

In Stage 2, the primary efficacy endpoint was analysed using the restricted maximum likelihood based mixed effects model with repeated measurements (MMRM) for the change from baseline of the selected CANTAB endpoints after 12 weeks of treatment. Descriptive statistics were used for safety parameters and other efficacy parameters.

Results

Surprisingly, a striking imbalance in both serious psychiatric adverse events and suicidality were noted in that 8/8 (100%) of psychiatric SAEs for hospitalization for disease worsening (i.e. schizophrenia, psychotic disorder), and suicidality leading to hospitalization were noted in the placebo arm versus none in any arm dosed with compound III (Table 9 in FIG. 7).

These SAEs occurred in subjects in the placebo arm across geographic regions, in both males and females taking a number of different antipsychotic medications.

These results show that by administration of compound III suicidal ideations, schizophrenia, relapses of schizophrenia and psychotic disorders can be successfully treated.

Further, the efficacy in the above mentioned indications may be supported by clinical trials described below for prevention/delay of first episode of psychosis and/or treatment of attenuated psychosis syndrome:

Prevention of Symptoms Leading to a First-Episode of Psychosis: Study Design, Inclusion Criteria of Patients, Statistical Method Regarding prevention of first episode of psychosis, the clinical trial disclosed below is in planning conducted to evaluate the efficacy, safety and tolerability of compound III given as an oral tablet during 52 weeks of treatment of 50 mg, twice daily (BID) compared to placebo in patients meeting diagnostic criteria for attenuated psychosis syndrome as defined in DSM-V. The study is designed to show superiority of compound III over placebo in preventing first episode of psychosis, as well as improvement in cognition and functional capacity.

The study is a multinational, multicentre, randomised, double-blind, placebo-controlled, parallel group design.

Study Medicine

Compound III (50 mg) and matching placebo is supplied as film-coated tablets (formulation 2).

Study Population

Patients who are ≥16 and ≤30 years old who meet diagnostic criteria for Attenuated Psychosis Syndrome (APS) per DSM-V as determined by the Structured Interview for Psychosis-Risk Syndromes (SIPS) will be screened using an algorithm developed by the North American Prodromal Longitudinal Study (NAPLS) consortia to select individuals predicted to be at greater than 35% risk of conversion to psychosis within the next 52 weeks.

Inclusion Criteria
1) Meet diagnostic criteria for attenuated psychosis syndrome as defined in DSM-V and determined by SIPS administered at screening, and diagnosis confirmed by Central Rating Committee after review of video-taped SIPS interview.
2) NAPLS risk calculator score ≥0.20 at screening indicative of greater than 35% risk of conversion to psychosis within the next 52 weeks.
3) Patients who are antipsychotic medication-naïve or who are currently taking an antipsychotic medication. If taking an antipsychotic medication, the dose can be decreased during the trial (or discontinued entirely), but the dose cannot be increased unless there is a significant worsening of psychosis symptoms.
4) Age ≥6 and ≤30 years at the time of consent/assent (if acceptable by local health authorities).

Exclusion Criteria
1) Present or past diagnosis of schizophrenia, schizophreniform, schizoaffective disorder, bipolar disorder I or II, or major depressive disorder with psychotic symptoms according to DSM-V.
2) Any suicidal behavior in the past 2 years (i.e. actual attempt, interrupted attempt, aborted attempt, or preparatory acts or behavior).
3) Any suicidal ideation of type 4 or 5 in the Columbia Suicide Severity Rating Scale (C-SSRS) in the past 3 months (i.e. active suicidal thought with intent but without specific plan, or active suicidal thought with plan and intent).
4) Known diseases of the central nervous system (including but not limited to any kind of seizures or stroke).
5) History of significant head injury (>5 minute without consciousness).
6) Diagnosis of a serious developmental disorder, mental retardation (documented IQ <70), cognitive disorder, or acute attenuated symptoms exclusively related to intoxication from a psychotropic substance.

Randomization

Patients eligible for the trial based on the aforementioned criteria may be assigned at random in a 1:1 ratio to one of 2 study arms (placebo bid, and 50 mg bid) and followed for 52 weeks of treatment.

Variables Assessed

The results of the primary and key secondary efficacy endpoints and the primary and secondary safety endpoints are summarized below.

Efficacy Endpoints

Primary Endpoint:

The primary endpoint is time to first episode of psychosis within a 52 week timeframe. First episode of psychosis defined as:

One or more of the following Positive Symptoms (Scale of Prodromal Symptoms (SOPS) criteria) in the psychotic range (rated at level 6):
Unusual Thought Content/Delusional Ideas
Suspiciousness/Persecutory Ideas
Grandiosity
Perceptual Abnormalities/Hallucinations
Disorganized Communication
AND either a symptom is seriously disorganizing or dangerous OR one of the symptoms above occurred at least one hour per day at an average frequency of four days/week over the past month.
OR
A new prescription or increase in dose of an ongoing antipsychotic medication for worsening of psychosis symptoms.

Time of onset of first episode psychosis is defined using the rater's best estimate as recorded in the Scale of Prodromal Symptoms (SOPS) interview or when the patient began taking a new prescription or increased the dose of antipsychotic medication.

Secondary Endpoints:
Change from baseline in everyday functional capacity as measured by Schizophrenia Cognition Rating Scale (SCoRS) total score after 24 and 52 weeks of treatment
Change from baseline in the neurocognitive composite score of Measurement and Treatment Research to Improve Cognition in Schizophrenia (MATRICS) Consensus Cognitive Battery (MCCB) after 24 and 52 weeks of treatment
Change from baseline in Positive and Negative Syndrome Scale (PANSS) positive items score, negative items score, and total score after 52 weeks of treatment.

Safety Endpoints

The primary safety endpoints are as follows:
Occurrence of adverse events (AEs)/serious adverse events (including the abnormalities of physical examination, vital signs, electrocardiogram test and laboratory tests)
Occurrence of protocol-specified adverse events of special interest
Dramatic worsening of disease state as assessed by PANSS
Suicidality as assessed by Columbia Suicidal Severity Rating Scale (C-SSRS)

The secondary safety endpoint is the change in psychopathology symptoms as assessed by PANSS.

Statistical Methods

For the primary endpoint of time to first episode of psychosis, the equality of the hazard rates will be tested by the Wald test for the treatment effect in a stratified Cox proportional hazards model at the two-sided 10% significance level. The model includes the treatment effect as the only covariate and is stratified by NAPLS risk calculator score and baseline use of antipsychotics. Secondary change from baseline endpoints will be analyzed using the restricted maximum likelihood (REML) based mixed effects model with repeated measurements (MMRM).

What is claimed is:

1. A crystalline form b of Compound III

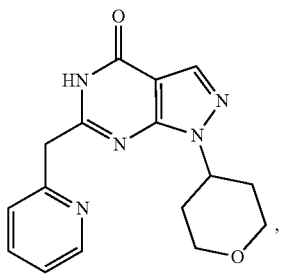

characterized by
   (i) an X-ray powder diffraction reflection peak having a 2-theta of 6.4° ±0.2°, wherein the X-ray powder diffraction reflections are measured using monochromatic CuKa1 radiation of λ=1.54056 Å, 40kV, 40mA, or
   (ii) a Raman spectrum having at least one characteristic peak at the following Raman shifts selected from the group consisting of 1182 ±2 $cm^{-1}$, 1394 ±2 $cm^{-1}$, and 1663 ±2 $cm^{-1}$.

2. The compound according to claim 1, further characterized by at least one additional X-ray powder diffraction reflection peak having a 2-theta value selected from the group consisting of 20.8° ±0.2°, 21.1° ±0.2°, 21.6° ±0.2°, 23.0° ±0.2°, 25.2° ±0.2°, and 12.9° ±0.2°.

3. The compound according to claim 1, wherein the compound exhibits a Raman spectrum comprising peaks at the following Raman shifts: 1182 ±2 $cm^{-1}$, 1394 ±2 $cm^{-1}$, and 1663 ±2 $cm^{-1}$.

4. A pharmaceutical composition comprising the compound of claim 1 and hydroxypropyl cellulose and/or croscarmellose sodium.

* * * * *